United States Patent
Landis

(10) Patent No.: US 11,864,603 B2
(45) Date of Patent: Jan. 9, 2024

(54) VISOR AND PROTECTIVE FACE SHIELD APPARATUS AND METHODS OF ASSEMBLY

(71) Applicant: OP-D-OP, INC., Roseville, CA (US)

(72) Inventor: Timothy J. Landis, Loomis, CA (US)

(73) Assignee: OP-D-OP, INC., Roseville, CA (US)

(*) Notice: Subject to any disclaimer, the term of this patent is extended or adjusted under 35 U.S.C. 154(b) by 0 days.

(21) Appl. No.: 17/105,577

(22) Filed: Nov. 26, 2020

(65) Prior Publication Data
US 2022/0125137 A1    Apr. 28, 2022

Related U.S. Application Data

(63) Continuation-in-part of application No. 29/755,787, filed on Oct. 22, 2020, now Pat. No. Des. 974,665.

(51) Int. Cl.
    *A41D 13/11*      (2006.01)
    *A42B 1/0182*     (2021.01)

(52) U.S. Cl.
    CPC ...... *A41D 13/1184* (2013.01); *A41D 13/1161* (2013.01); *A42B 1/0182* (2021.01)

(58) Field of Classification Search
    CPC ........... A42B 3/22; A42B 3/221; A42B 3/225; A42B 1/0182; A42B 1/242; A42B 3/127; A41D 13/1184; A61F 9/027; F21V 21/088
    See application file for complete search history.

(56) References Cited

U.S. PATENT DOCUMENTS

| | | | |
|---|---|---|---|
| 1,333,102 A | | 3/1920 | Dietsche |
| 2,004,098 A | | 6/1935 | Andrews |
| 2,728,913 A | * | 1/1956 | Connor ................. A42B 3/225 2/10 |
| 2,927,411 A | | 3/1960 | Kerr |
| 2,975,953 A | * | 3/1961 | Muth .................. B65D 5/6667 229/149 |
| 3,945,044 A | * | 3/1976 | McGee .................. A61F 9/025 2/436 |
| 4,192,017 A | * | 3/1980 | Fay ...................... A42B 1/0182 2/12 |
| 4,475,254 A | * | 10/1984 | Bay ....................... A42B 3/227 2/12 |
| 4,701,965 A | * | 10/1987 | Landis ..................... A61F 9/02 2/428 |
| 4,821,340 A | * | 4/1989 | Johnson ................. A61F 9/029 351/158 |
| 4,850,049 A | * | 7/1989 | Landis .................. A42B 1/012 2/10 |

(Continued)

OTHER PUBLICATIONS

"Portion" The Free Dictionary by Farlex. Web. https://www.thefreedictionary.com/portion.*

(Continued)

*Primary Examiner* — Jillian K Pierorazio
(74) *Attorney, Agent, or Firm* — O'BANION & RITCHEY LLP; John P. O'Banion

(57) ABSTRACT

A visor and protective face shield apparatus having a transparent or non-transparent visor and a transparent face shield. The visor and face shield can be assembled from separate components or from a unitary blank using improved tabs and slots such that the face shield is supported by the visor.

18 Claims, 10 Drawing Sheets

(56) References Cited

U.S. PATENT DOCUMENTS

| | | | | |
|---|---|---|---|---|
| 4,852,186 A | * | 8/1989 | Landis | A41D 13/1184 2/9 |
| 4,864,653 A | * | 9/1989 | Landis | A42B 1/0181 2/9 |
| 4,920,576 A | * | 5/1990 | Landis | A41D 13/1184 2/9 |
| 4,945,573 A | * | 8/1990 | Landis | A41D 13/1184 2/9 |
| D395,391 S | * | 6/1998 | Landis | D9/415 |
| 6,959,988 B1 | * | 11/2005 | Sheldon | G02C 1/04 351/103 |
| 9,532,617 B2 | * | 1/2017 | Miller | A41D 13/1184 |
| 10,278,866 B2 | * | 5/2019 | Moore | A61F 9/028 |
| 10,571,714 B2 | * | 2/2020 | Chen | G02C 1/10 |
| D898,567 S | | 10/2020 | Kennedy | |
| 11,147,323 B1 | * | 10/2021 | Wilson | A42B 1/0182 |
| 2005/0218201 A1 | * | 10/2005 | Billig | B65D 5/6608 229/122 |
| 2006/0109420 A1 | * | 5/2006 | Holm | G02C 3/02 351/153 |
| 2009/0079931 A1 | * | 3/2009 | Yang | G02C 9/00 351/60 |
| 2009/0190089 A1 | * | 7/2009 | Wang | G02C 1/04 351/106 |
| 2012/0272483 A1 | * | 11/2012 | Moore | F16B 2/22 24/3.12 |
| 2014/0196199 A1 | * | 7/2014 | Huffman | A42B 3/20 2/421 |
| 2015/0049294 A1 | * | 2/2015 | Chin | G02C 5/08 351/86 |
| 2015/0223540 A1 | * | 8/2015 | Daniels | A42B 3/221 224/272 |
| 2015/0272784 A1 | * | 10/2015 | Padovani | A61F 9/029 2/436 |
| 2018/0020760 A1 | * | 1/2018 | Mayerovitch | A42B 3/06 2/411 |
| 2019/0001737 A1 | * | 1/2019 | Mullen | B43K 23/001 |
| 2021/0030095 A1 | * | 2/2021 | Reicher | A42C 1/06 |
| 2021/0345720 A1 | * | 11/2021 | Snow | A42B 3/18 |

OTHER PUBLICATIONS

ISA/EPO, European Patent Office (EPO), International Search Report and Written Opinion dated Feb. 11, 2022, related PCT international application No. PCT/US2021/056025, pp. 1-11, with claims searched, pp. 12-15.

* cited by examiner

VISOR AND PROTECTIVE FACE SHIELD APPARATUS AND METHODS OF ASSEMBLY

CROSS-REFERENCE TO RELATED APPLICATIONS

This application is a continuation-in-part of U.S. design patent application Ser. No. 29/755,787 filed on Oct. 22, 2020, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to personal protection devices that cover a portion of the user's face, and more particularly to a visor and face shield apparatus that provides protection to the wearer from exposure to germs, viruses other contaminants.

2. Background Discussion

Masks made from gauze and paper or from fabric materials are well known devices that can be worn by a person in an effort to prevent exposure to germs, viruses other contaminants and to prevent spread to others. However, wearing such masks can be hot and uncomfortable, and putting the masks on and removing them can be time-consuming and sometimes difficult. Furthermore, breath can condense within the mask and hence the mask can become saturated with moisture which results in the mask failing to be an effective barrier to viruses and bacteria. The condensation can also cause fogging of eyeglasses worn by the user. Furthermore, masks can cause the wearer to re-inhale exhaled breath causing the $CO_2$ content of the blood to rise. The result of this may be increased heart and respiration rates and higher body temperatures and perspiration.

Alternatives to conventional mask include visor and face shield devices such as those described in U.S. Pat. Nos. 4,852,176 and 4,864,643 both of which are incorporated herein by reference in their entireties. Those devices address the problems with conventional masks but can be difficult to assemble by a user.

BRIEF SUMMARY

This disclosure describes improved visor and protective face shield apparatuses and assembly mechanisms.

In one embodiment, a visor and protective face shield apparatus comprises (a) a transparent or non-transparent visor and (b) a transparent face shield. In this embodiment, the visor and face shield are separate components that are easily assembled using improved tabs and slots such that the face shield is supported by the visor. In one embodiment, the visor has arms which are adjustable to fit the head size of the wearer. In one embodiment, a forehead support member is provided.

In another embodiment, a visor and protective face shield apparatus comprises (a) a transparent or non-transparent visor and (b) a transparent face shield that is integral with the visor. In this embodiment, the visor and face shield are formed initially as a unitary flat blank. To assemble the apparatus, the face shield is bent with respect to the visor and secured into place using improved tabs and slots such that the visor supports the face shield. In one embodiment, the visor has arms which are adjustable to fit the head size of the wearer. In one embodiment, a forehead support member is provided.

In all embodiments, when the apparatus is assembled and placed on the wearer's head, the visor preferably supports the face shield and the face shield extends downward from the visor. The face shield also preferably extends down to below the level of the wearer's mouth and around the sides of the wearer's face, thus providing superior, frontal and lateral protection from contaminants. It will be appreciated that a face shield that is supported by a visor and which extends downward therefrom when assembled or worn can also be said to "depend" from the visor.

In one embodiment, the face shield is connected to the visor and secured into place using an innovative tab and slot mechanism. In one embodiment, the visor has an edge and a plurality of slots positioned distal of the edge. In one embodiment, the face shield has an edge and a plurality of tabs that extend from the edge of the face shield. The tabs and slots are configured such that a tab can easily be bent and inserted into a corresponding slot and, after, the tab is inserted, the automatically springs back to its original flat position to secure the face shield to the visor.

In one embodiment, the slots have a straight central portion and angled portions positioned at each end of the straight central portion. In one embodiment, the edge of the face shield is partially "undercut" beneath each tab. Undercuts span from the sides of the tabs toward the central axis through the tab wherein the tab appears "tree-shaped" with a trunk portion and adjacent side portions, with the "undercuts" forming notches in the face shield positioned beneath each of the side portions of the tab. This configuration facilitates greater ease of tab insertion and assembly of the apparatus and, further, provides for a more secure connection between the visor and the face shield.

Another aspect of the technology is that flat tabs with the undercuts facilitate ease of manufacturing.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
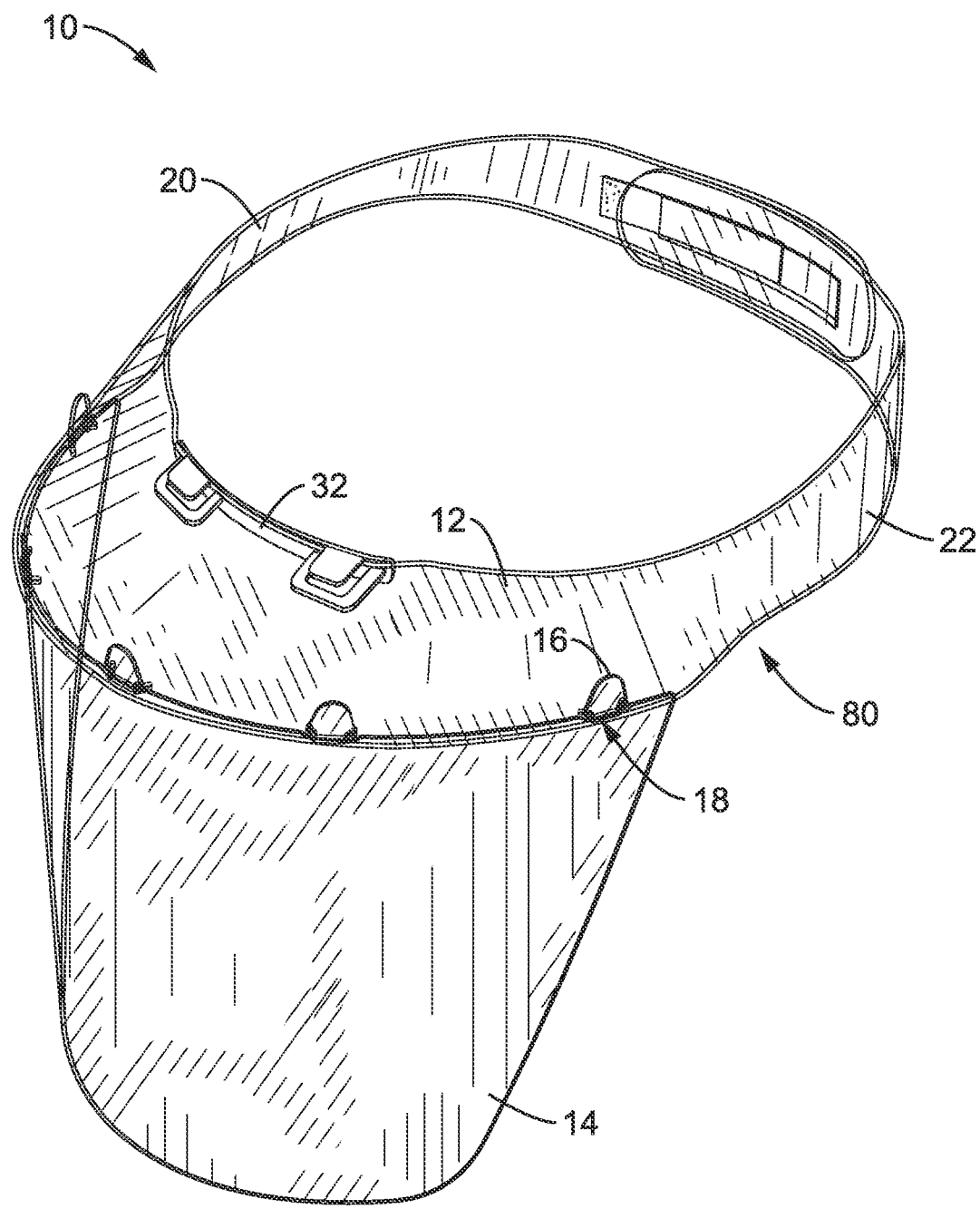
FIG. 1 is an assembled perspective view of a visor and protective face shield apparatus according to an embodiment of the technology presented herein.

A. Visor and Face Shield Assembled from Separate Components

Referring first to FIG. 1 through FIG. 12, in one embodiment a visor and protective face shield apparatus 10 comprises a transparent, non-transparent, or tinted visor 12 and a transparent or tinted face shield 14. In this embodiment, the visor and face shield are separate components that are easily assembled using improved tabs 16 and slots 18 such that the face shield is supported by the visor.

It will be appreciated that various means can be provided for supporting the visor on a wearer's head. For example, in one embodiment, a head support means comprises a pair of arms 20, 22 that can be joined at overlapping end portions 24, 26. The end portions of the arms may be brought around the back of the wearer's head and fastened to together in such a way as to adjust to the head size of the wearer. In one embodiment, the arms can be shorter so that the ends do not overlap and an elastic band that extends from the end portion of one arm to the end portion of the other arm can be used instead of joining overlapping end portions as described above. In other words, the support means can be a combination of arms and an elastic band, strap or other stretchable mechanism. In other embodiments the length of the arms can vary, and each arm can have a different length in relation to the other arm. For example, the support means can be comprising a long arm that extends from one side of the visor, wraps around the wearer's head, and connects to short "stub" arm on the other side of the visor.

In one embodiment, the end portions of the arms are connected together using connection means such as hook and loop fastener strips 28, 30. It will be appreciated, however, that other connection means such as hooks, snaps, buckles, adhesive strips, ties, buttons, tabs and slots, and other connectors known to those skilled in the art can be used. In the preferred embodiment the connection means is reversible so that the end portions of the arms can be joined and separated as desired.

Also, in one embodiment a forehead support member 32 is provided. The forehead support member is preferably made from a rigid or semi-rigid material and has a rearward facing surface 34 to which is attached a cushion 36. The cushion may be made of, for example, a soft rubberized or foam material that will provide a comfortable surface that rests against the user's forehead (not shown). The cushion is preferably attached to using an adhesive material. Alternatively the forehead support member can be made from a soft rubberized material or the like that provides an integral cushion.

Figure 2:
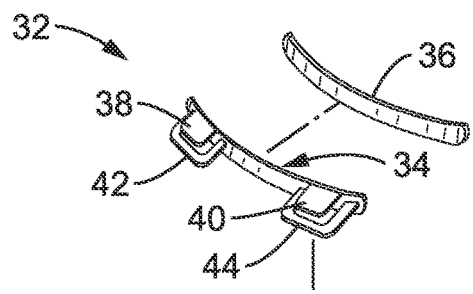
FIG. 2 is an exploded view of the apparatus of FIG. 1.
Figure 3:
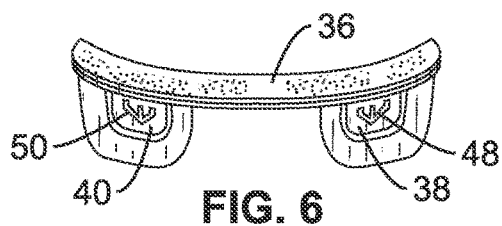
FIG. 3 is a detail view of a cutout for retaining the forehead support member illustrated in FIG. 1 and FIG. 2.
Figure 6:
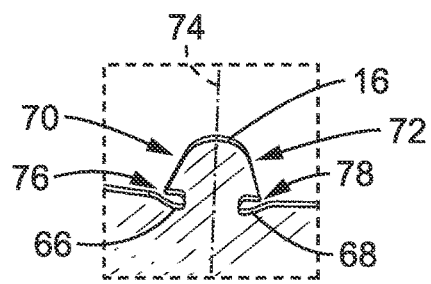
FIG. 6 is a assembled bottom view of the forehead support member shown in FIG. 2.

Referring more specifically to FIG. 2, FIG. 3 and FIG. 6 together, in one embodiment the forehead support member includes a pair of forward-facing upper tabs 38, 40 spaced apart from lower frames 42, 44, respectively. The spaces between the upper tabs and lower frames are configured to receive portions of the rear edge 46 of the visor such that the edge of the visor slides into the spaces and the tabs and frames slide over the edge of the visor. To prevent movement and secure the forehead support member in place in relation to the visor, the undersides of the tabs include protrusions 48, 50 (here shown as arrow-shaped) that fit into and mate with corresponding cutouts 52, 54 (here shown as triangular-shaped). It will be appreciated that the protrusions and cutouts could have other shapes as well and perform the same or substantially similar function.

For purposes of this description, it will be appreciated that terms such as "upper", "lower", "forward", "rearward", "outward", "inward", "front", "back", "top", "bottom", and "side" may be used to denote relative orientations, such as in the context of an assembled apparatus or when the apparatus is positioned on the wearer's head, and are not positional requirements per se.

Figure 4:
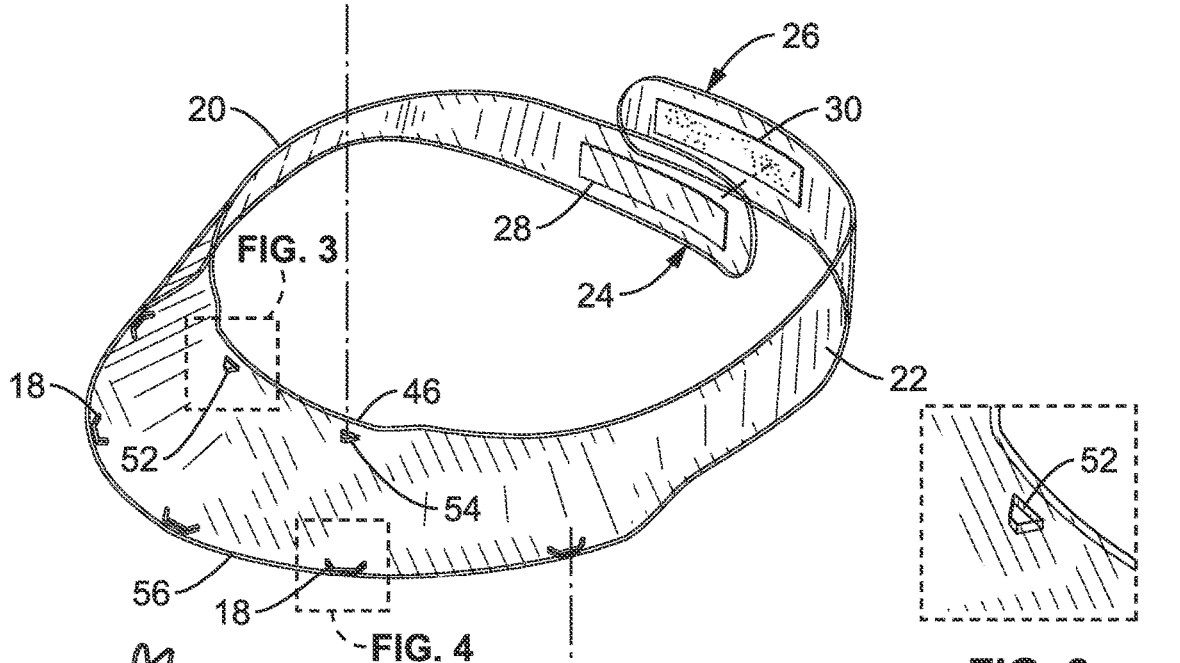
FIG. 4 is a detail view of a connecting slot according to an embodiment of the technology presented herein.
Figure 5:
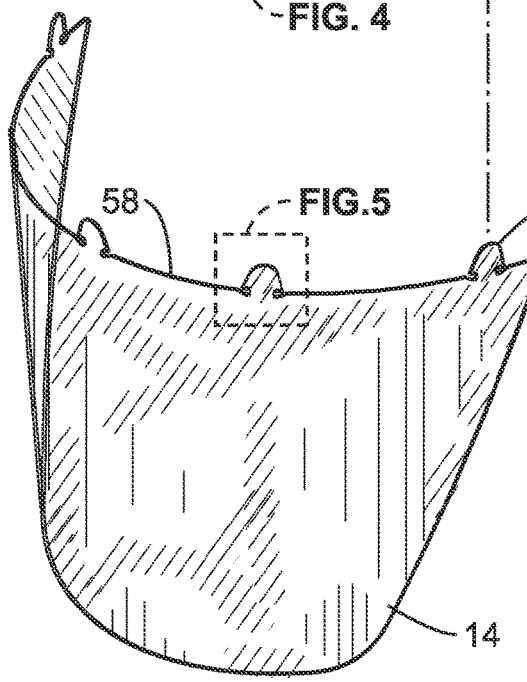
FIG. 5 is a detail view of a connecting tab according to an embodiment of the technology presented herein.

Referring more particularly to FIG. 2, FIG. 4 and FIG. 5, in one embodiment the face shield is secured to the visor using an innovative tab and slot mechanism. In one embodiment, the visor has a forward edge 56 and a plurality of slots 16 positioned along the edge and inward of the edge. In the embodiment shown, five slots are provided but the number of slots can vary. In one embodiment, the face shield has an upper edge 58 and a plurality of tabs 16 that extend from the upper edge of the face shield. In the embodiment shown, five tabs are provided to correspond to the number of slots but the number of tabs can vary as the number of corresponding tabs vary.

The tabs and slots are configured such that a tab can easily be bent and inserted into a corresponding slot and, after, the tab is inserted, the tab automatically springs back to its original flat position to secure the face shield to the visor. It will be appreciated that a tab can be "bent" by any form of deformation that changes its shape from flat to arcuate, such as, for example, by the user bending the tab with his or her fingers or sliding the flat tab into the slot wherein the shape of the slot bends the tab. As illustrated in FIG. 4 this is facilitated by, in one embodiment, configuring the slots such that they have slots have a straight central portion 60 and angled portions 62, 64 positioned at each end of the straight central portion.

As illustrated in FIG. 5, in one embodiment, the upper edge of the face shield is partially "undercut" beneath each tab. Undercuts 66, 68 span from the sides 70, 72 of a tab toward the central axis 74 through the tab such that the tab appears "tree-shaped" with the undercuts forming a pair of "notches" 76, 78 in the face shield positioned beneath each tab. In one embodiment (not shown) the notch is beneath a tab on only side of the tab. In another embodiment, some tabs can have both notches and some tabs can have only one notch.

In one embodiment (not shown) there is a slit or a notch in the tab that extends along the central axis from the tip of the tab toward the upper edge of the face shield, whereby "ears" are formed that assist with tab insertion. The slit or notch need not extend the entire distance from the tip of the tab to the edge of the visor.

It will be appreciated that the above-described configuration of slots and tabs facilitates greater ease of tab insertion and assembly of the apparatus and, further, provides for a more secure connection between the visor and the face shield.

In one embodiment the arms may include an arcuate recess 80 in the area that will rest above the wearer's ears. The arms may be formed in various widths, lengths, and other dimensions. The visor and face shield may be formed in various dimensions as well.

Figure 7:
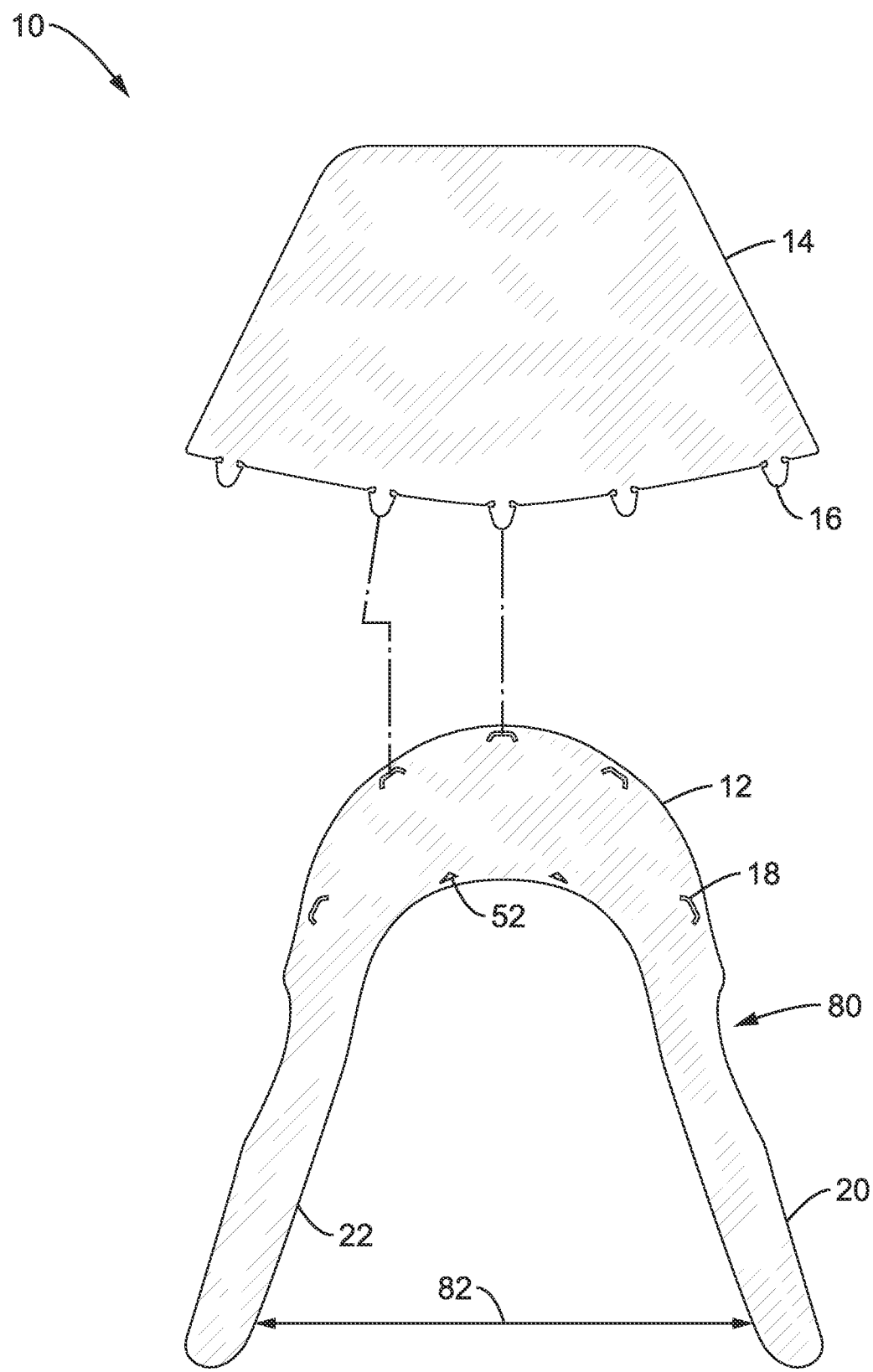
FIG. 7 is a plan view of the visor and face shield of FIG. 1 and FIG. 2 prior to assembly and showing separate components, and showing a wide arm spacing according to an embodiment of the technology presented herein.
Figure 8:
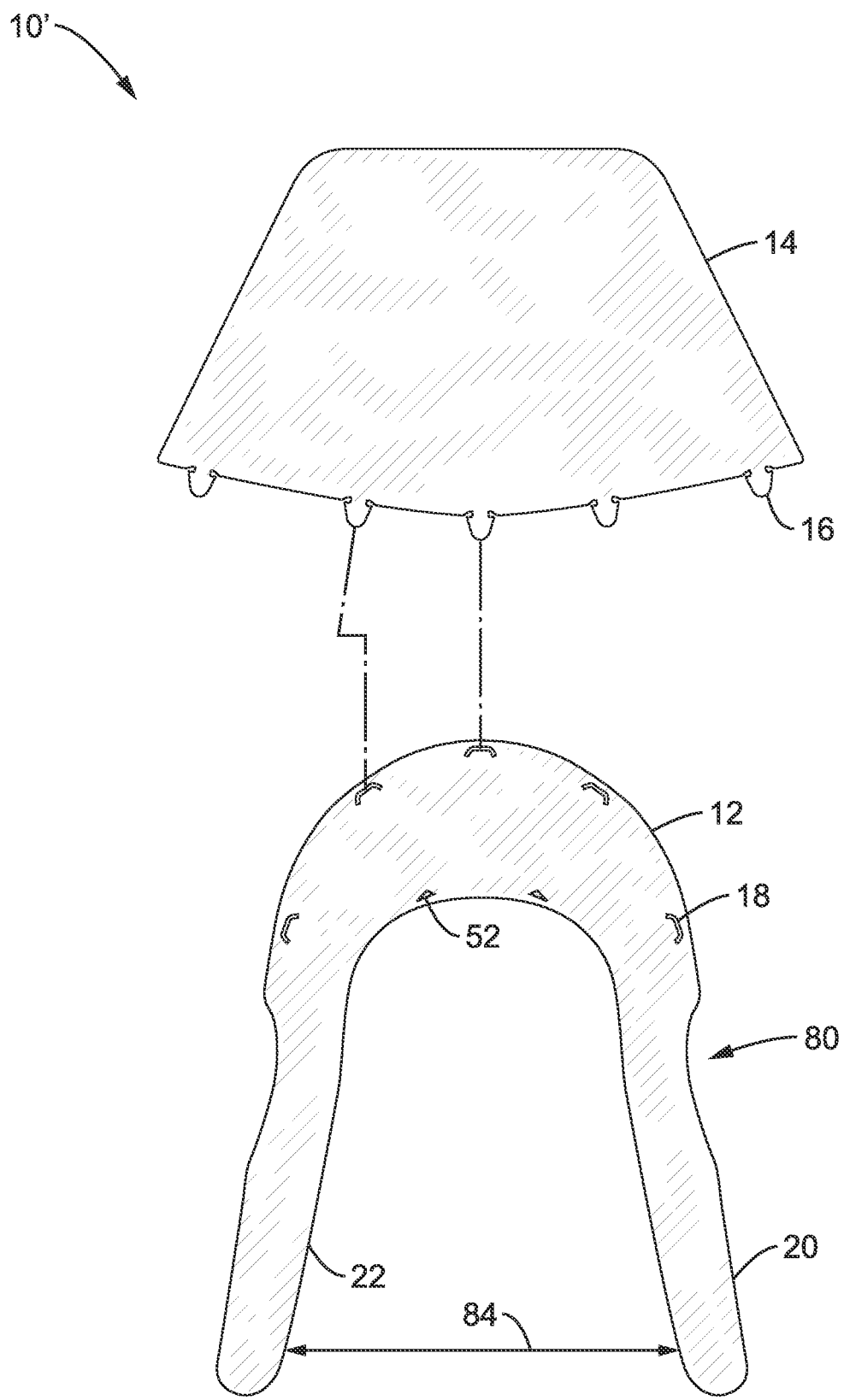
FIG. 8 is a plan view of the visor and face shield of FIG. 1 and FIG. 2 prior to assembly and showing separate components, and showing a narrow arm spacing according to an embodiment of the technology presented herein.

In one embodiment the face shield and visor are formed as components that are initially flat as illustrated in FIG. 7 and FIG. 8. The visor and face shield can be, for example, fabricated by stamping from flat sheets of material, thus avoiding more expensive techniques such as injection molding and various fabricating techniques. The flat components are then assembled by folding, twisting and/or bending as required.

In various embodiments, the spread of the arms can vary. FIG. 7 illustrates an example of a wider spread 82 in relation to a narrower spread 84 illustrated in FIG. 8. An advantage of a wider spread is that the forehead support member is more elevated and the slope of the visor (forehead support member to the front edge of visor) has a greater angle than with a narrow spread such the visor provides more shade over the wearer's eyes. The wider the spread, the more pronounced the downward slope.

Figure 9:
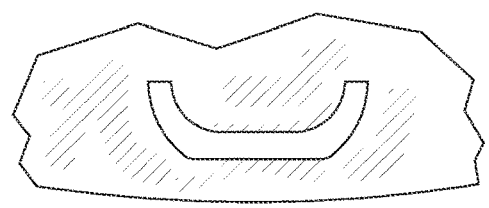
FIG. 9 is a closeup view of a slot according to an embodiment of the technology presented herein.
Figure 10:
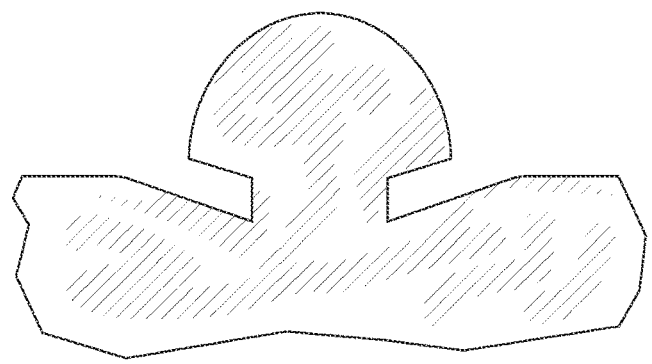
FIG. 10 through FIG. 12 are closeup views of different tab configurations according to embodiments of the technology presented herein.
Figure 11:
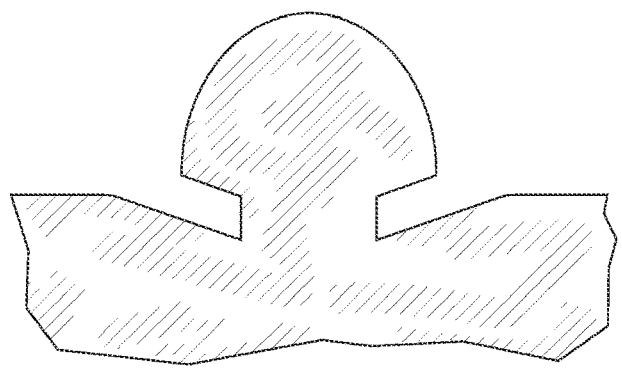
Figure 12:
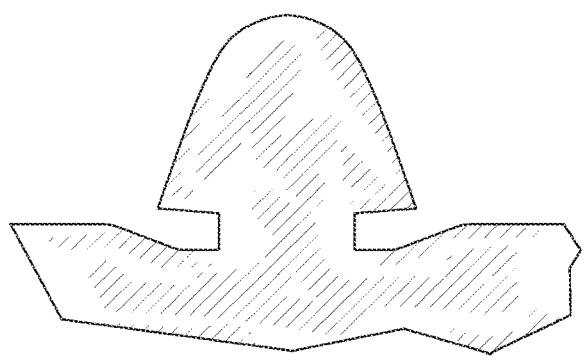
Figure 13:
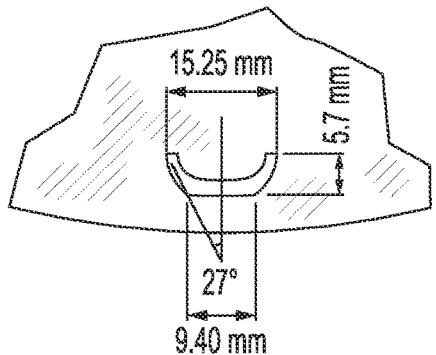
FIG. 13 through FIG. 22 illustrate examples of different slot and tab configurations and dimensions according to embodiments of the technology presented herein.
Figure 16:
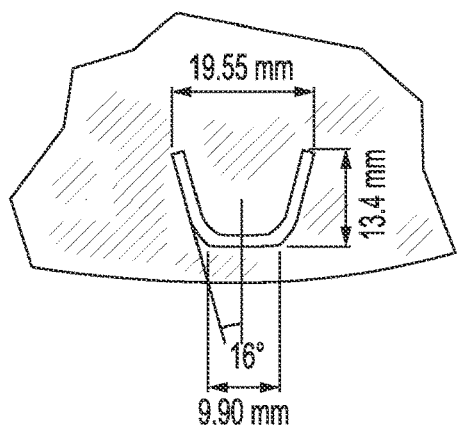
Figure 14:
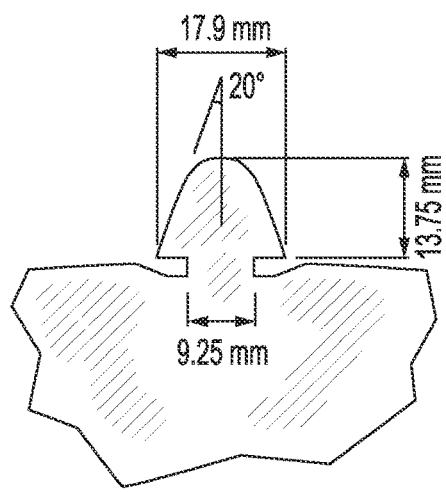
Figure 17:
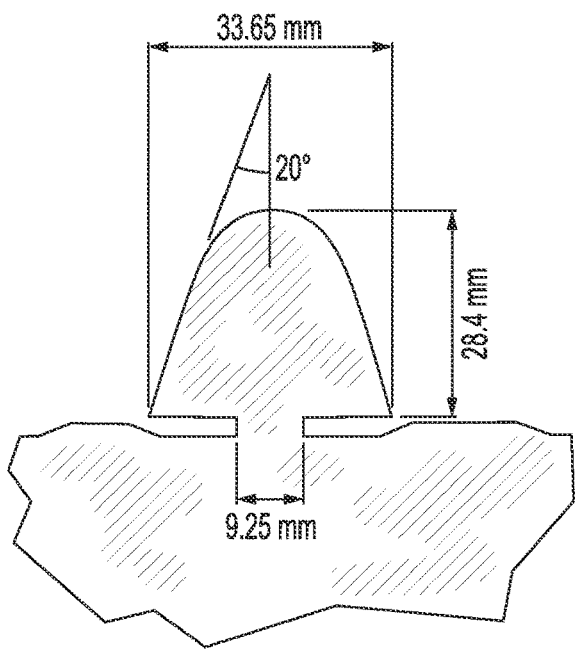
Figure 15:
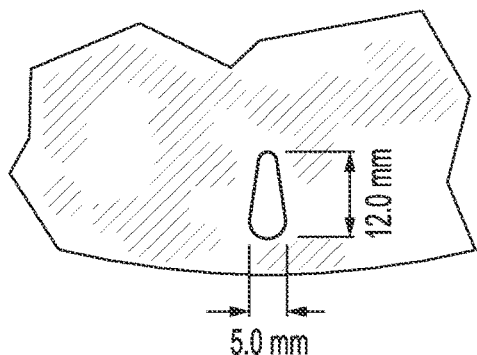
Figure 18:
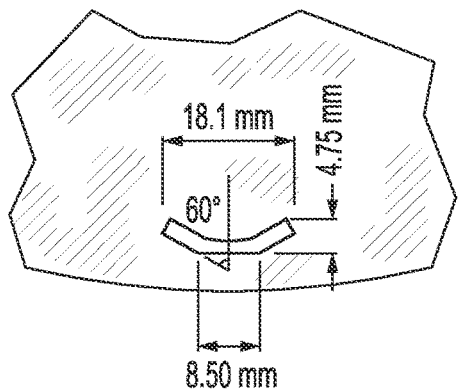
Figure 19:
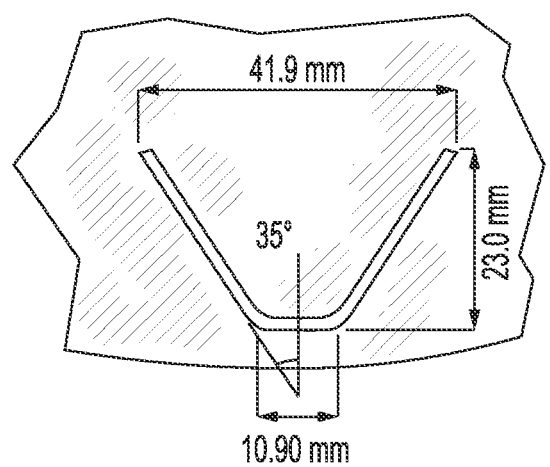
Figure 20:
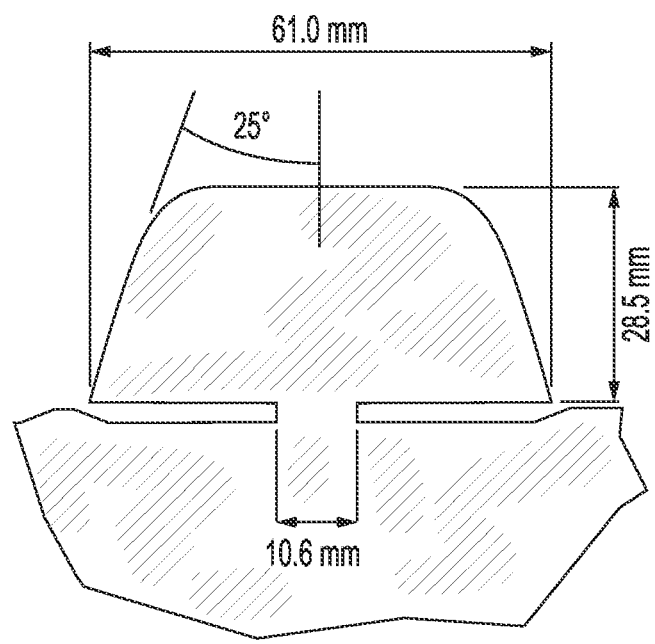
Figure 21:
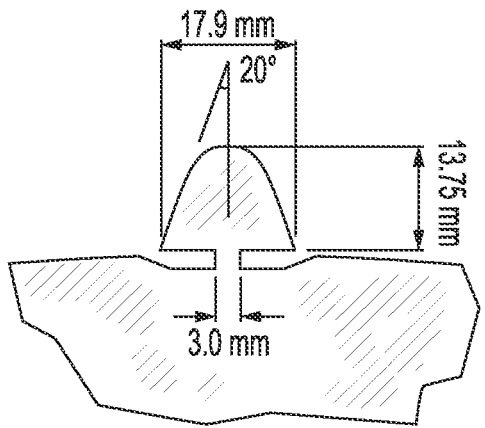
Figure 22:
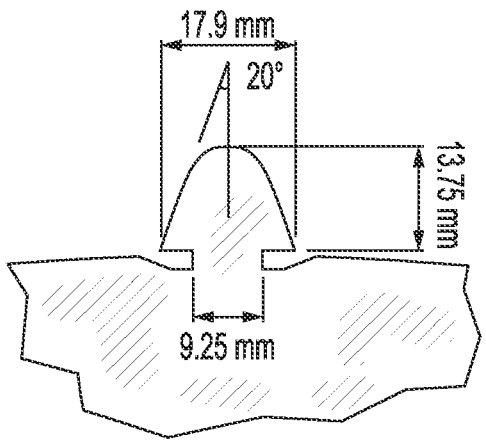

It will be appreciated that the shapes of the tabs and slots may vary. FIG. 9 illustrates a slot with ends that are slightly more rounded than shown in FIG. 4. The important feature of the slots are that they are not merely straight from end to end but have angled portions at each of a central straight portion as previously described. FIG. 10 through FIG. 12 illustrate that the shapes of the tabs may vary as well, with "mushroom-shaped" tabs of different sizes illustrated in FIG. 10 and FIG. 11 and a "tree-shaped" tab illustrated in FIG. 12. FIG. 13 through FIG. 22 illustrate various shapes and provide sample dimensions of slots and tabs.

In all embodiments, when the apparatus is assembled and placed on the wearer's head, the visor preferably supports the face shield and the face shield extends downward from the visor. The face shield also preferably extends down to below the level of the wearer's mouth and around the sides of the wearer's face, thus providing superior, frontal and lateral protection from contaminants. It will be appreciated that a face shield that is supported by a visor and which extends downward therefrom when assembled or worn can also be said to "depend" from the visor.

The visor and face shield can be formed from various synthetic materials such as plastic, cross-linked polycarbonate, mylar, acetate or other material that is flexible. The thickness of the material can also vary to control flexibility, resilience, and strength. The visor may be made transparent or in various colors or tints. The visor may also carry ornamental graphics or text which are applied to the visor like decals, or stamped, or printed, or silkscreened, or applied onto the visor in conventional ways. The face shield is preferably transparent but can be tinted or colored, and may also carry ornamental graphics or text, provided that the wearer's vision is not obscured to an undesirable degree.

B. Univisor

Figure 23:
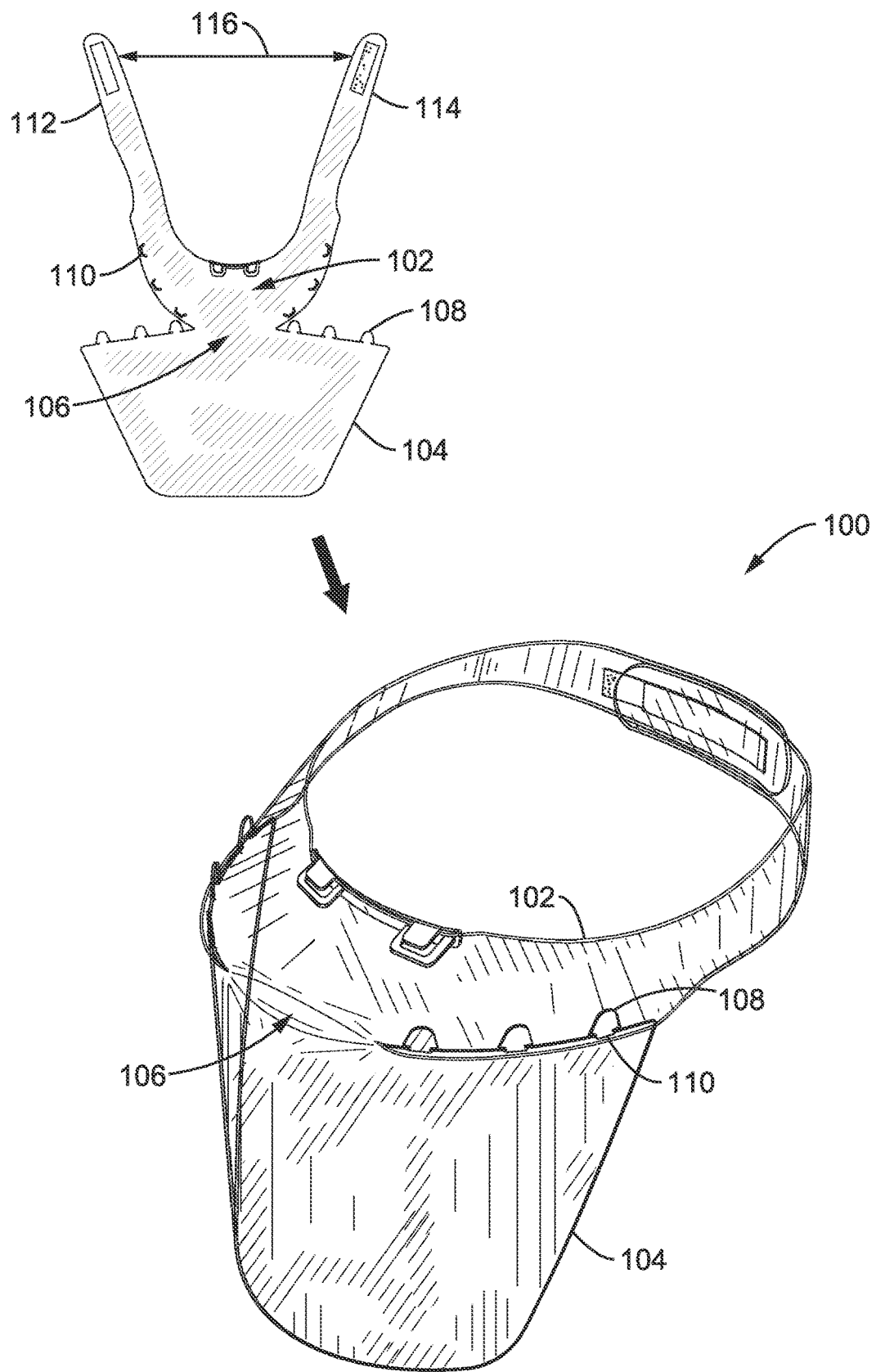
FIG. 23 shows a plan view of a unitary visor and face shield blank with wide arm spacing along with a perspective view of visor and face shield assembled from the blank according to an embodiment of the technology presented herein.
Figure 24:
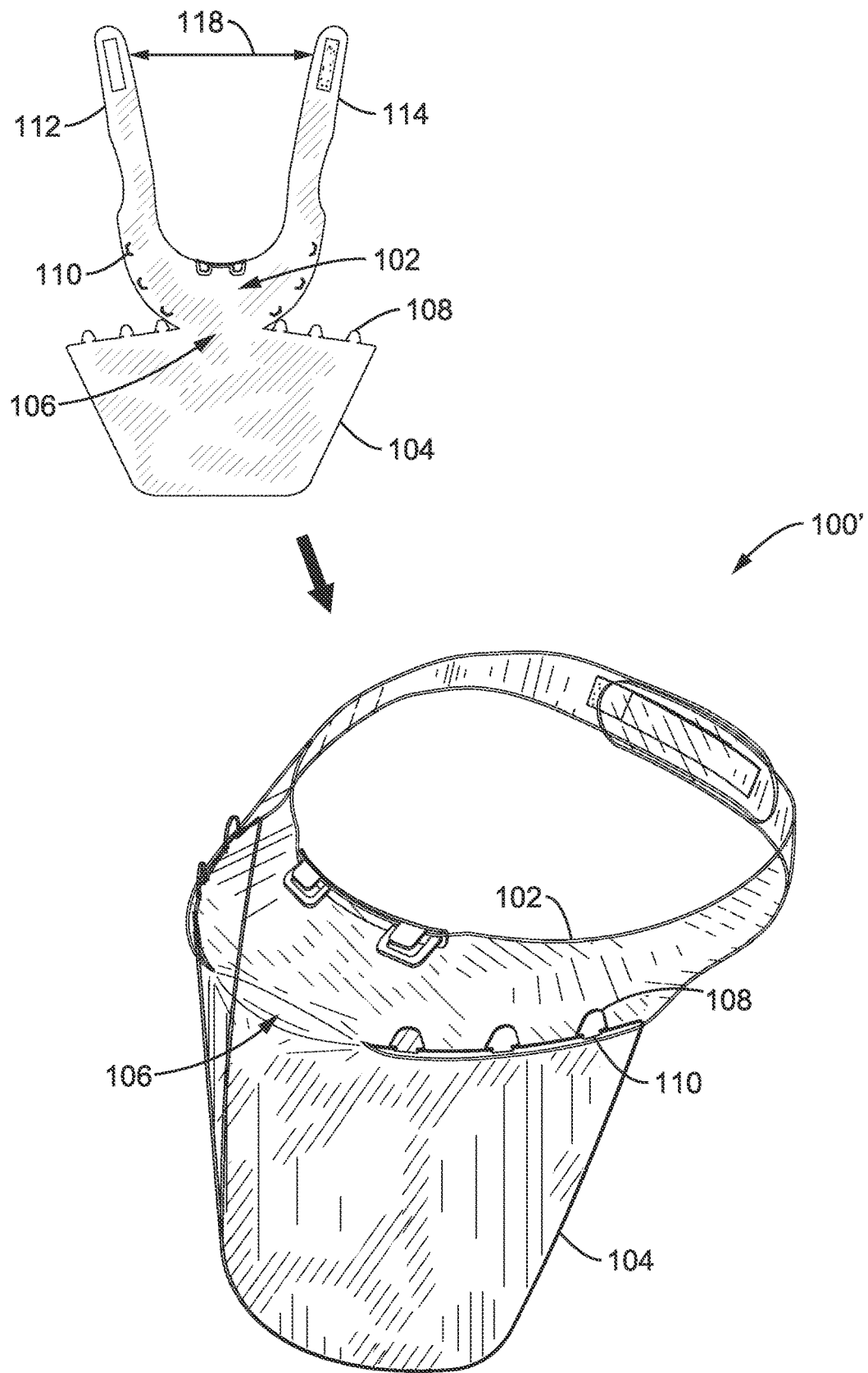
FIG. 24 shows a plan view of a unitary visor and face shield blank with narrow arm spacing along with a perspective view of visor and face shield assembled from the blank according to an embodiment of the technology presented herein.

FIG. 23 and FIG. 24 illustrate an embodiment of a visor and protective face shield apparatus 100 that is formed from a unitary flat blank instead of using separate components as described above. To assemble the apparatus, the face shield is bent with respect to the visor and secured to the visor using the previously-described improved tabs and slots such that the visor supports the face shield.

More particularly, in one embodiment, assembly involves bending the visor portion 102 at an approximate right angle in relation to the face shield portion 104 along a "hinge" area 106. Thereafter, tabs 108 are inserted through corresponding slots 110. In the embodiment shown, six tabs and slots are used but the number can vary.

In various embodiments, the spread of the arms 112, 114 can vary. FIG. 23 illustrates an example of a wider spread 116 in relation to a narrower spread 118 illustrated in FIG. 24. In other respects, the apparatus 100 is the same as apparatus 10 described above.

C. Visor and Face Shield Improvements

It will be appreciated from the foregoing that the slots and tabs described herein can be used with any visor and protective face shield apparatus the face shield needs to be secured to the visor. Accordingly, in one embodiment, an improvement to a visor and face shield apparatus comprises a plurality of slots spaced apart along an edge of a visor and positioned inward in relation to the edge of the visor; and a plurality of tabs spaced apart along an edge of a face shield and extending outward from the edge of the face shield, said plurality of tabs corresponding to said plurality of slots; wherein each said slot has a substantially straight central portion and angled end portions extending from the central portion; wherein the edge of the face shield is undercut in areas beneath each side of a tab to form a notch beneath each side of the tab; wherein each tab is insertable into a corresponding slot by bending the tab from a flat position to an arcuate position; and wherein each tab automatically springs back to the flat position after insertion, whereby the visor and face shield are secured together.

D. Slot and Tab Joinery Method

It will further be appreciated that an improved joinery method has been developed. In one embodiment the method comprises providing a plurality of slots spaced apart along an edge of a first component and inward in relation to the edge of the first component; providing a plurality of tabs spaced apart along an edge of a second component and extending outward from the edge of the second component, said plurality of tabs corresponding to said plurality of slots; wherein each said slot has a substantially straight central portion and angled end portions extending from the central portion; wherein the edge of the second component is undercut in areas beneath each side of a tab to form a notch beneath each side of the tab; and bending each tab from a flat position to an arcuate position and inserting the tab into a corresponding slot; wherein each tab automatically springs back to the flat position after insertion, whereby the first and second components are secured together.

Therefore, from the description herein it will be appreciated that the present disclosure encompasses multiple embodiments which include, but are not limited to, the following:

1. A visor and protective face shield apparatus, the apparatus comprising: (a) a visor having a plurality of slots spaced apart along an edge of the visor and positioned inward in relation to the edge of the visor, each said slot having a substantially straight central portion and angled end portions extending from the central portion; and (b) a face shield having a plurality of tabs spaced apart along an edge of the face shield and extending from the edge of the face shield, said plurality of tabs corresponding to said plurality of slots; (c) wherein the edge of the face shield is undercut in an area beneath each tab to form a notch beneath a side of the tab; (d) wherein each tab is insertable into a corresponding slot by the tab bending from a flat position to an arcuate position; and (e) wherein each tab automatically springs back to the flat position after insertion.

2. The apparatus of any preceding or following embodiment, wherein the edge of the face shield is undercut in areas beneath each side of a tab to form a notch beneath each side of the tab.

3. The apparatus of any preceding or following embodiment, further comprising means for supporting the visor on a wearer's head.

4. The apparatus of any preceding or following embodiment, further comprising a forehead support member that is attachable to the visor.

5. The apparatus of any preceding or following embodiment, wherein the tabs and slots secure the face shield together such that the face shield depends from the visor when worn.

6. The apparatus of any preceding or following embodiment, wherein the visor and face shield are separate components.

7. The apparatus of any preceding or following embodiment, wherein the visor and face shield are a unitary component.

8. The apparatus of any preceding or following embodiment, wherein the visor includes an ornamental graphic image.

9. A visor and protective face shield apparatus, the apparatus comprising: (a) a visor; and (b) a face shield; (c) the visor having a plurality of slots spaced apart along an edge of the visor and positioned inward in relation to the edge of the visor; (d) the face shield having a plurality of tabs spaced apart along an edge of the face shield and extending outward from the edge of the face shield, said plurality of tabs corresponding to said plurality of slots; (e) wherein each said slot has a substantially straight central portion and angled end portions extending from the central portion; (f) wherein the edge of the face shield is undercut in an area beneath each tab to form a notch beneath a side of the tab; (g) wherein each tab is insertable into a corresponding slot by the tab bending from a flat position to an arcuate position; and (h) wherein each tab automatically springs back to the flat position after insertion, whereby the face shield and visor are secured together and the face shield depends from the visor when worn.

10. The apparatus of any preceding or following embodiment, further comprising means for supporting the visor on a wearer's head.

11. The apparatus of any preceding or following embodiment, wherein the edge of the face shield is undercut in areas beneath each side of a tab to form a notch beneath each side of the tab.

12. The apparatus of any preceding or following embodiment, further comprising a forehead support member that is attachable to the visor.

13. The apparatus of any preceding or following embodiment, wherein the visor and face shield are separate components.

14. The apparatus of any preceding or following embodiment, wherein the visor and face shield are a unitary component.

15. The apparatus of any preceding or following embodiment, wherein the visor includes an ornamental graphic image.

16. In a visor and protective face shield apparatus, an improvement comprising: a plurality of slots spaced apart along an edge of a visor and positioned inward in relation to the edge of the visor; a plurality of tabs spaced apart along an edge of a face shield and extending outward from the edge of the face shield, said plurality of tabs corresponding to said plurality of slots; wherein each said slot has a substantially straight central portion and angled end portions extending from the central portion; wherein the edge of the face shield is undercut in an area beneath each tab to form a notch beneath a side of the tab; wherein each tab is insertable into a corresponding slot by the tab bending from a flat position to an arcuate position; and wherein each tab automatically springs back to the flat position after insertion, whereby the visor and face shield are secured together.

17. The improved apparatus of any preceding or following embodiment, wherein the edge of the face shield is undercut in areas beneath each side of a tab to form a notch beneath each side of the tab.

18. A method of joining components, the method comprising: providing a plurality of slots spaced apart along an edge of a first component and inward in relation to the edge of the first component; providing a plurality of tabs spaced apart along an edge of a second component and extending outward from the edge of the second component, said plurality of tabs corresponding to said plurality of slots; wherein each said slot has a substantially straight central portion and angled end portions extending from the central portion; wherein the edge of the second component is undercut in an area beneath each tab to form a notch beneath a side of the tab; bending each tab from a flat position to an arcuate position and inserting the tab into a corresponding slot; wherein each tab automatically springs back to the flat position after insertion, whereby the first and second components are secured together.

19. The method of any preceding embodiment, wherein the edge of the second component is undercut in areas beneath each side of a tab to form a notch beneath each side of the tab.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing group of elements, indicates that at least one of these group elements is present, which includes any possible combination of these listed elements as applicable.

References in this specification referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

As used herein, the term "set" refers to a collection of one or more objects. Thus, for example, a set of objects can include a single object or multiple objects.

As used herein, the terms "approximately", "approximate", "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A visor and protective face shield apparatus, the apparatus comprising:
   (a) a visor having a plurality of slots spaced apart along a forward edge of the visor and positioned inward in relation to the forward edge of the visor, each said slot having a substantially straight central portion and angled end portions extending from the central portion; and
   (b) a face shield having a plurality of tabs spaced apart along an edge of the face shield and extending from the edge of the face shield, said plurality of tabs corresponding to said plurality of slots, each said tab configured for aligning and fixing the tab with the corresponding slot;
   (c) wherein the edge of the face shield has an undercut in an area beneath each said tab to form a notch beneath a side of said tab extending inward from the edge of the face shield;
   (d) wherein each said tab is insertable into a corresponding slot by said tab bending from a flat position to an arcuate position; and
   (e) wherein each said tab automatically springs back to the flat position after insertion, thereby locking each tab within the slot;
   (f) wherein each said undercut spans from sides of the corresponding tab toward a central axis through the tab wherein the tab is tree-shaped with a trunk portion and adjacent side portions, with the undercut forming a notch in the face shield positioned beneath each of the side portions of the tab.

2. The apparatus of claim 1, wherein the edge of the face shield is undercut in areas beneath each side of each said tab to form a notch beneath each side of said tab extending inward from the edge of the face shield.

3. The apparatus of claim 1, further comprising means for supporting the visor on a wearer's head.

4. The apparatus of claim 1, further comprising a forehead support member that is attachable to the visor, the forehead support member configured for attachment to a rearward edge of the visor, the forehead support member comprising a pair of forward-facing upper tabs and a corresponding pair of lower frames, wherein the upper tabs and lower frames have spaces therebetween that are configured to receive portions of the rearward edge of the visor such that the rearward edge of the visor slides into said spaces and the upper tabs and lower frames slide over the rearward edge of the visor, wherein the upper tabs have undersides with protrusions configured to fit into corresponding cutouts in the visor to secure the forehead support member in place in relation to the visor.

5. The apparatus of claim 1, wherein said plurality of tabs and slots secure the face shield together such that the face shield depends from the visor when worn.

6. The apparatus of claim 1, wherein the visor and face shield are separate components.

7. The apparatus of claim 1, wherein the visor and face shield are a unitary component.

8. The apparatus of claim 1, wherein the visor includes an ornamental graphic image.

9. A visor and protective face shield apparatus, the apparatus comprising:
   (a) a visor; and
   (b) a face shield;

(c) the visor having a plurality of slots spaced apart along a forward edge of the visor and positioned inward in relation to the forward edge of the visor;

(d) the face shield having a plurality of tabs spaced apart along an edge of the face shield and extending outward from the edge of the face shield, said plurality of tabs corresponding to said plurality of slots;

(e) wherein each said slot has a substantially straight central portion and angled end portions extending from the central portion;

(f) wherein the edge of the face shield is undercut in an area beneath each said tab to form a notch beneath a side of said tab extending inward from the edge of the face shield;

(g) wherein each said tab is insertable into a corresponding slot by said tab bending from a flat position to an arcuate position; and (h) wherein each said tab automatically springs back to the flat position after insertion, whereby the face shield and visor are secured together and the face shield depends from the visor when worn;

(i) wherein each said undercut spans from sides of the corresponding tab toward a central axis through the tab wherein the tab is tree-shaped with a trunk portion and adjacent side portions, with the undercut forming a notch in the face shield positioned beneath each of the side portions of the tab.

10. The apparatus of claim 9, further comprising means for supporting the visor on a wearer's head.

11. The apparatus of claim 9, wherein the edge of the face shield is undercut in areas beneath each side of each said tab to form a notch beneath each side of said tab extending inward from the edge of the face shield.

12. The apparatus of claim 9, further comprising a forehead support member that is attachable to the visor, the forehead support member configured for attachment to a rearward edge of the visor, the forehead support member comprising a pair of forward-facing upper tabs and a corresponding pair of lower frames, wherein the upper tabs and lower frames have spaces therebetween that are configured to receive portions of the rearward edge of the visor such that the rearward edge of the visor slides into said spaces and the upper tabs and lower frames slide over the rearward edge of the visor, wherein the upper tabs have undersides with protrusions configured to fit into corresponding cutouts in the visor to secure the forehead support member in place in relation to the visor.

13. The apparatus of claim 9, wherein the visor and face shield are separate components.

14. The apparatus of claim 9, wherein the visor and face shield are a unitary component.

15. The apparatus of claim 9, wherein the visor includes an ornamental graphic image.

16. In a visor and protective face shield apparatus, an improvement comprising:

a plurality of slots spaced apart along a forward edge of a visor and positioned inward in relation to the forward edge of the visor;

a plurality of tabs spaced apart along an edge of a face shield and extending outward from the edge of the face shield, said plurality of tabs corresponding to said plurality of slots;

wherein each said slot has a substantially straight central portion and angled end portions extending from the central portion;

wherein the edge of the face shield is undercut in an area beneath each said tab to form a notch beneath a side of said tab extending inward from the edge of the face shield;

wherein each said tab is insertable into a corresponding slot by said tab bending from a flat position to an arcuate position; and wherein each said tab automatically springs back to the flat position after insertion, whereby the visor and face shield are secured together;

wherein each said undercut spans from sides of the corresponding tab toward a central axis through the tab wherein the tab is tree-shaped with a trunk portion and adjacent side portions, with the undercut forming a notch in the face shield positioned beneath each of the side portions of the tab.

17. The improved apparatus of claim 16, wherein the edge of the face shield is undercut in areas beneath each side of each said tab to form a notch beneath each side of said tab.

18. The improved apparatus of claim 16, further comprising:

a forehead support member that is attachable to the visor;

the forehead support member configured for attachment to a rearward edge of the visor;

the forehead support member comprising a pair of forward-facing upper tabs and a corresponding pair of lower frames;

wherein the upper tabs and lower frames have spaces therebetween that are configured to receive portions of the rearward edge of the visor such that the rearward edge of the visor slides into said spaces and the upper tabs and lower frames slide over the rearward edge of the visor;

wherein the upper tabs have undersides with protrusions configured to fit into corresponding cutouts in the visor to secure the forehead support member in place in relation to the visor.

* * * * *